United States Patent
Zimmer et al.

(10) Patent No.: US 6,890,952 B2
(45) Date of Patent: May 10, 2005

(54) CYCLIC SUBSTITUTED AMINOMETHYL COMPOUNDS AND MEDICAMENTS COMPRISING THESE COMPOUNDS

(75) Inventors: Oswald Karl Zimmer, Wuerselen (DE); Babette-Yvonne Koegel, Langerwehe-Hamich (DE); Wolfgang Werner Alfred Strassburger, Wuerselen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/339,671

(22) Filed: Jan. 10, 2003

(65) Prior Publication Data

US 2003/0166708 A1 Sep. 4, 2003

Related U.S. Application Data

(63) Continuation of application No. PCT/EP01/07750, filed on Jul. 6, 2001.

(30) Foreign Application Priority Data

Jul. 10, 2000 (DE) .......................................... 100 33 459

(51) Int. Cl.⁷ ....................... A61K 31/35; C07D 311/04
(52) U.S. Cl. ....................................... 514/456; 549/407
(58) Field of Search ........................... 514/456; 549/407

(56) References Cited

U.S. PATENT DOCUMENTS

| | | | |
|---|---|---|---|
| 3,956,391 A | 5/1976 | Houlihan et al. | |
| 6,013,809 A | 1/2000 | Zimmer et al. | |
| 6,022,895 A | 2/2000 | Zimmer et al. | |

FOREIGN PATENT DOCUMENTS

DE     0 922 703 B1    12/2002

OTHER PUBLICATIONS

International Search Report.

*Primary Examiner*—Deborah C Lambkin
(74) *Attorney, Agent, or Firm*—Crowell & Moring LLP

(57) ABSTRACT

Cyclic substituted aminomethyl compounds of general formula IA and IB, methods for production thereof, intermediates in said production methods, a medicament containing at least one of said cyclic substituted aminomethyl compounds, the use of said cyclic substituted aminomethyl compounds for the production of a medicament, pharmaceutical compositions containing said compounds, and methods for the treatment of pain, incontinence, pruritis, tinnitus aurium and/or diarrhea using said pharmaceutical compositions.

28 Claims, No Drawings

CYCLIC SUBSTITUTED AMINOMETHYL COMPOUNDS AND MEDICAMENTS COMPRISING THESE COMPOUNDS

CROSS REFERENCE TO RELATED APPLICATIONS

The present application is a continuation of international patent application no. PCT/EP01/07750, filed Jul. 6, 2001, designating the United States of America and published in German as WO 02/08218, the entire disclosure of which is incorporated herein by reference. Priority is claimed based on Federal Republic of Germany patent application no. 100 33 459.8, filed Jul. 10, 2000.

BACKGROUND OF THE INVENTION

The present Application relates to cyclic substituted aminomethyl compounds, processes for their preparation, intermediate compounds of these processes, medicaments comprising at least one of the cyclic substituted aminomethyl compounds, the use of the cyclic substituted aminomethyl compounds for the preparation of a medicament for treatment of pain, urinary incontinence, itching, tinnitus aurium and/or diarrhea, and pharmaceutical compositions comprising these compounds.

Treatment of chronic and non-chronic states of pain is of great importance in medicine. There is a world-wide need for therapies which have a good action for target-orientated treatment of chronic and non-chronic states of pain appropriate for the patient, by which is to be understood successful and satisfactory pain treatment for the patient.

Conventional opioids, such as morphine, have a good action in the treatment of severe to very severe pain. However, their use is limited by the known side effects, such as respiratory depression, vomiting, sedation, constipation and development of tolerance. Furthermore, they are less active on neuropathic or incidental pain, from which tumor patients in particular suffer.

Opioids display their analgesic action by binding to receptors on the membrane which belong to the family of so-called G protein-coupled receptors (GPCR). Biochemical and pharmacological characterization of, for example, $\mu$-, $\kappa$- and $\delta$-subtypes of these receptors has aroused the hope that subtype-specific opioids have a different action/side effects profile to the conventional opioids, such as morphine. Morphine binds selectively to the so-called $\mu$-receptors. On the other hand, compounds with an antinociceptive potential are known which do not bind or scarcely bind to $\mu$-receptors and the analgesic action of which is mediated exclusively or predominantly via $\delta$-receptors.

DE 197 55 480 A1 thus discloses substituted heterocyclic benzocycloalkenes, the analgesic activity of which is mediated largely or exclusively via $\delta$-receptors. Substituted amino compounds with a corresponding biological activity are known from DE 198 05 370 A1.

DESCRIPTION OF THE INVENTION

The present invention is based on the object of providing compounds which have an analgesic action and are suitable for pain treatment—in particular also for treatment for chronic and neuropathic pain. These substances moreover should as far as possible cause none of the side effects which usually occur when opioids with $\mu$-receptor affinity are used, such as nausea, vomiting, dependency, respiratory depression or constipation.

This object is achieved by cyclic substituted aminomethyl compounds of formula IA or IB which, in accordance with the object, show no or only a low affinity for $\mu$-receptors and moreover surprisingly have an analgesic action in vivo, even though in vitro they show no specific activity on opiate $\delta$-receptors either.

The compounds according to the invention are cyclic substituted aminomethyl compounds of formula IA or IB.

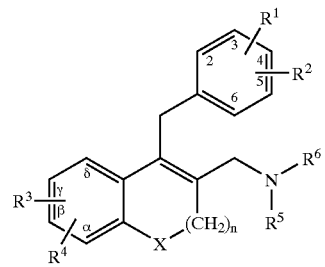

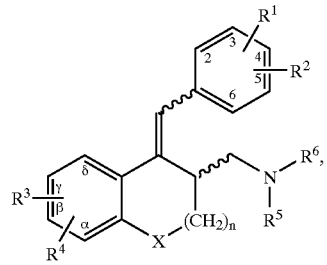

wherein
R$^1$ denotes H, F, Cl, OH, O—CH$_3$, O—(C$_{2-6}$-alkyl), O—(C$_{3-7}$-cycloalkyl), CH$_3$, C$_{2-6}$-alkyl, CH$_2$F, CHF$_2$ or CF$_3$, in each case in the 2-, 3-, 4-, 5- or 6-position of the phenyl ring, R$^2$ denotes H, F, Cl, CH$_3$, C$_{2-6}$-alkyl, CH$_2$F, CHF$_2$ or CF$_3$, in each case in the 2-, 3-, 4-, 5- or 6-position of the phenyl ring, R$^3$ and R$^4$ independently of one another denote H, F, Cl, OH, O—CH$_3$, O—(C$_{2-6}$-alkyl), O—(C$_{3-7}$-cycloalkyl), CH$_3$, C$_{2-6}$-alkyl, CH$_2$F, CHF$_2$, CF$_3$, O-aryl, aryl or heterocyclyl, in each case in the $\alpha$-, $\beta$-, $\gamma$- and/or $\delta$-position of the aromatic ring, R$^5$ and R$^6$ independently of one another denote CH$_3$, C$_{2-6}$-alkyl, C$_{3-7}$-cycloalkyl, CH$_2$-(C$_{3-7}$-cycloalkyl), aryl, (C$_{1-6}$-alkyl)-aryl, heterocyclyl or (C$_{1-6}$-alkyl)-heterocyclyl, X denotes CH$_2$, O, S, SO or SO$_2$, n is 0, 1, 2 or 3 if X denotes CH$_2$, and is 1, 2 or 3 if X denotes O, S, SO or SO$_2$, and the configuration of the exocyclic double bond in compounds of formula IB is E or Z, and their pharmaceutically acceptable salts.

The compounds according to the invention show, without affinity for $\mu$-receptors, a significant analgesic action without at the same time having a specific activity on $\delta$-receptors. The manner in which the compounds according to the invention mediate their analgesic action and via which opiate receptor subtypes may do so has not yet been clarified.

The term "C$_{2-6}$-alkyl" in the context of this invention includes acyclic saturated or unsaturated hydrocarbon radicals, which can be branched- or straight-chain and unsubstituted or mono- or polysubstituted, having 2, 3, 4, 5 or 6 carbon atoms, i.e. C$_{2-6}$-alkanyls, C$_{2-6}$-alkenyls and C$_{2-6}$-alkinyls. C$_{2-6}$-Alkyl is advantageously chosen from the group which comprises ethyl, n-propyl, 2-propyl, n-butyl, iso-butyl, sec-butyl, tert-butyl, n-pentyl, iso-pentyl, neopentyl, n-hexyl, 2-hexyl; ethylenyl (vinyl), ethinyl, propenyl (—CH$_2$CH=CH$_2$, —CH=CH—CH$_3$, —C(=CH$_2$)—CH$_3$), propinyl (—CH—C=CH), butenyl, butinyl, pentenyl, pentinyl, hexenyl and hexinyl.

The term "C$_{3-7}$-cycloalkyl" for the purpose of this invention denotes cyclic hydrocarbons having 3, 4, 5, 6 or 7 carbon atoms, which can be saturated or unsaturated, unsubstituted or mono- or polysubstituted. C$_{3-7}$-Cycloalkyl is advantageously chosen from the group which comprises cyclopropyl, cyclobutyl, cyclopentyl, cyclohexyl, cycloheptyl, cyclopentenyl, cyclohexenyl and cycloheptenyl.

The term "aryl" in the context of this invention denotes, inter alia, phenyls, naphthyls or anthracenyls. The aryl radicals can also be fused with further saturated, (partly) unsaturated or aromatic ring systems. Each aryl radical can be present in unsubstituted or mono- or polysubstituted form, it being possible for the substituents on the aryl to be in any desired position of the aryl. Aryl is advantageously chosen from the group which comprises, phenyl, p-toluyl, p-methoxyphenyl, xylyl, 1-naphthyl, 2-naphthyl and 4-biphenyl. Preferred substituents are OH, F, Cl, Br, C$_{1-6}$-alkyl, C$_{3-7}$-cycloalkyl, CH$_2$F, CHF$_2$, CF$_3$, O—C$_{1-6}$-alkyl, O—C$_{3-7}$-cycloalkyl, O—CH$_2$—C$_{3-7}$-cycloalkyl, heterocyclyl, phenyl and naphthyl.

The term "heterocyclyl" represents a 5-, 6- or 7-membered cyclic organic radical which contains at least 1, optionally also 2, 3, 4 or 5 heteroatoms, it being possible for the heteroatoms to be identical or different and for the cyclic radical to be saturated, unsaturated or aromatic, unsubstituted or mono- or polysubstituted. The heterocyclic radical can also be part of a bi- or polycyclic system. Preferred heteroatoms are nitrogen, oxygen and sulfur. It is preferable for the heterocyclyl radical to be chosen from the group which comprises pyrrolyl, furyl, thienyl, pyrazolyl, imidazolyl, pyridinyl, pyridazinyl, pyrimidinyl, pyrazinyl, pyranyl, indolyl, indazolyl, purinyl, pyrimidinyl, indolizinyl, quinolinyl, isoquinolinyl, quinazolinyl, carbazolyl, phenazinyl, phenothiazinyl, pyrrolidinyl, piperidinyl, piperazinyl and morpholinyl, wherein the bonding to the nitrogen atom by the aryl ring(s), the phenyl ring or the aromatic ring of the compounds of formulae IA and IB according to the invention may be via any desired ring member of the heterocyclyl radical.

The terms "C$_{1-6}$-alkyl-aryl" and "C$_{1-6}$-alkyl-heterocyclyl" for the purpose of the present invention mean that C$_{1-6}$-alkyl, aryl and heterocyclyl have the meanings defined above and are bonded to the aromatic ring or the nitrogen atom of the aminomethyl radical of the compounds of the formula IA and/or IB via a C$_{1-6}$-alkyl group.

In connection with "alkyl", "alkanyl", "alkenyl" and "alkinyl", the term "substituted" is understood in the context of this invention as meaning the replacement of a hydrogen radical by F, Cl, Br, I, NH$_2$, SH or OH, polysubstituted radicals being understood as meaning those radicals which are substituted several times, e.g. twice or three times, both on different and on the same atoms, for example three times on the same C atom, as in the case of CF$_3$ or —CH$_2$CF$_3$, or at different places, as in the case of —CH(OH)—CH=CH—CHCl$_2$. Polysubstitution can be with identical or with different substituents.

In respect of "aryl", "alkyl-aryl", "heterocyclyl", "alkyl-heterocyclyl" and "cycloalkyl" or "CH$_2$—(C$_{3-7}$-cycloalkyl)", in the context of this invention "mono- or polysubstituted" is understood as meaning one or more, e.g. two, three or four, replacements of one or more hydrogen atoms of the ring system by F, Cl, Br, I, NH$_2$, SH, OH, CF$_3$, NO$_2$, SO$_3$H, C(O)OH; =O or =S; mono- or polysubstituted or unsubstituted C$_{1-6}$-alkanyl, C$_{2-6}$-alkenyl, C$_{2-6}$-alkinyl, O—C$_{1-6}$-alkyl, —C(O)O—C$_{1-6}$-alkyl, —C$_{1-6}$-alkyl-C(O)O—C$_{1-6}$-alkyl; mono- or polysubstituted or unsubstituted phenyl, benzyl, naphthyl or heterocyclyl; on one or optionally different atoms. The polysubstitution here is with identical or with different substituents.

The radicals R$^1$ and R$^2$ can in each case be provided in the 2-, 3-, 4-, 5- or 6-position of the phenyl ring, i.e. in the ortho-, meta- or para-position.

The radicals R$^3$ and R$^4$ can in each case be provided in the α-, β-, γ- or δ-position of the aromatic ring.

X in the compounds of the formulae IA and IB according to the invention denotes CH$_2$ (methylene), O (oxygen), S (sulfur), SO (sulfoxide) or SO$_2$ (sulfone), while n is 0, 1, 2 or 3 in the case where X denotes CH$_2$ or is 1, 2 or 3 in the case where X denotes O, S, SO or SO$_2$. If X=CH$_2$, the compounds of formulae IA and IB are indane or indene derivatives (n=0), dihydro- or tetrahydronaphthalene derivatives (n=1), benzocycloheptyl derivatives (n=2) or benzocyclooctyl derivatives (n=3). If X represents oxygen or sulfur, the compounds according to the invention are e.g. for n=2 oxepine or thiepine derivatives respectively. If X=SO, cyclic sulfoxides are present, and if X=SO$_2$, cyclic sulfones are present.

The cyclic substituted aminomethyl compounds of formula IB according to the invention can be either in the E or in the Z configuration or as a mixture of the two configurations. For the purpose of this invention, E configuration is understood as meaning that stereochemical arrangement in which the phenyl ring substituted by R$^1$ and R$^2$ and the aromatic ring substituted by R$^3$ and R$^4$ are trans with respect to one another, while in the Z configuration the two rings are arranged cis with respect to one another:

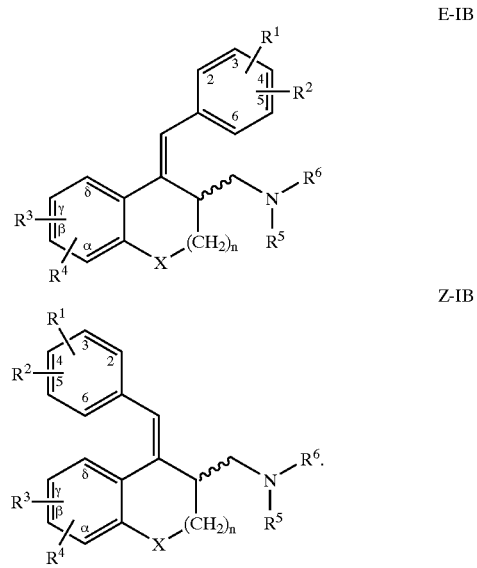

Pharmaceutically acceptable salts in the context of this invention are those salts of the compounds according to formulae IA or IB according to the invention which are physiologically tolerated for pharmaceutical applications—in particular during use on mammals, especially on humans. Such pharmaceutically acceptable salts can be formed, for example, with inorganic or organic acids, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The salts formed are, inter alia, hydrochlorides, hydrobromides, phosphates, carbonates, bicarbonates, formates, acetates, oxalates, succinates, tartrates, fumarates, citrates and glutamates. The hydrates of the compounds according to the invention, which can be obtained e.g. by crystallization from aqueous solution, are also preferred.

A group of preferred compounds of the present invention is formed by those cyclic substituted aminomethyl compounds of formula IA in which, independently of one another, $R^1$ denotes OH, O—$CH_3$ or Cl, $R^2$ denotes H or Cl, $R^3$ denotes H or OH, $R^4$ denotes H, $R^5$ and $R^6$ denote $CH_3$ and X denotes $CH_2$, O, S or SO and n is 1 or 2, and their pharmaceutically acceptable salts. Particularly preferred compounds of formula IA here are those in which, independently of one another, $R^1$ denotes 3-OH, 2-O—$CH_3$, 3-O—$CH_3$ or 4-Cl, $R^2$ denotes H, 2-Cl or 4-Cl, $R^3$ denotes H, α-OH or β-OH, $R^4$ denotes H, $R^5$ and $R^6$ denote $CH_3$ and X denotes $CH_2$, O, S or SO and n is 1 or 2, and pharmaceutically acceptable salts thereof.

Another group of preferred compounds of the present invention is formed by those cyclic substituted aminomethyl compounds of formula IB in which $R^1$ denotes OH, O—$CH_3$ or Cl; $R^2$, $R^3$ and $R^4$ denote H; $R^5$ and $R^6$ denote $CH_3$; X denotes $CH_2$, O or S; n is 1 or 2 and the configuration of the exocyclic double bond is E or Z, and their pharmaceutically acceptable salts. Particularly preferred cyclic substituted aminomethyl compounds of the formula IB here are those in which $R^1$ is 3-OH, 2-O—$CH_3$, 3-O—$CH_3$ or 4-Cl, $R^2$, $R^3$ and $R^4$ are H; $R^5$ and $R^6$ are $CH_3$ and X is $CH_2$, O or S, n is 1 or 2 and the configuration of the exocyclic double bond is E or Z, and their pharmaceutically acceptable salts.

It is moreover preferable that the compounds of formula IA or IB according to the invention are in the form of a mixture of the isomers with an endocyclic and exocyclic double bond, i.e. as a mixture of compounds which differ only in the position of the aliphatic double bond in the ring containing the group X or outside the ring containing the group X, but in which the definition of $R^1$ or $R^6$, X and n coincides. The ratio of isomers in this mixture can vary. The ratio of the endo and exo compounds of the formulae IA and IB e.g. can be in a range from 100:1 to 1:100. The ratio is preferably 1:1, 1:2, 2:1, 1:10, 10:1, 1:100 or 100:1.

The compounds of formula IA or IB according to the invention can be —where they are optically active substances—in the form of their racemates, in the form of the pure enantiomers and/or diastereomers or in the form of mixtures of these enantiomers or diastereomers, and in particular both in substance and as pharmaceutically acceptable salts of these compounds. This applies in particular to compounds of formula IB which always have an asymmetric centre in the allylic position, marked with an asterisk *, to the exocyclic double bond:

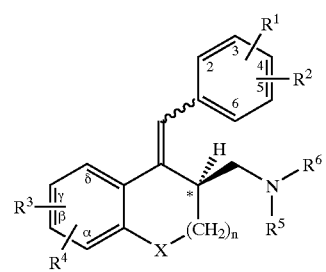

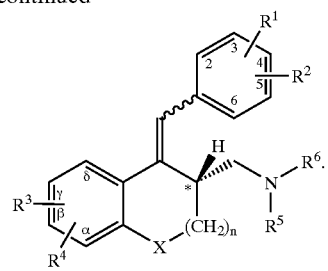

The mixtures can be in any desired mixing ratio of the enantiomers or diastereomers contained in them. The compounds according to the invention or their pharmaceutically acceptable salts are preferably in the enantiomerically pure form.

The following compounds according to the invention are particularly preferred:

[1-(4-chlorobenzyl)-3,4-dihydro-naphth-2-ylmethyl]-dimethylamine, 3-(2-dimethylaminomethyl-3,4-dihydro-naphth-1-ylmethyl)-phenol, 5-(4-chlorobenzyl)-6-dimethylaminomethyl-7,8-dihydro-naphth-1-ol, E-(5RS)-[5-(4-chlorobenzylidene)-6,7,8,9-tetrahydro-5H-benzocyclohepten-6-ylmethyl]-dimethylamine, Z-(4RS)[5-(4-chlorobenzylidene)-2,3,4,5-tetrahydrobenzo[b]oxepin-4-ylmethyl]dimethylamine, 3-(4-dimethylaminomethyl-2,3-dihydro-benzo[b]oxepin-5-ylmethyl)-phenol, E-(4RS)-3-(4-dimethylaminomethyl-3,4-dihydro-2H-benzo[b]oxepin-5-ylidenemethyl)-phenol or Z-(4RS)-3-(4-dimethylaminomethyl-3,4-dihydro-2H-benzo[b]oxepin-5-ylidenemethyl)-phenol, and their pharmaceutically acceptable salts, in particular their hydrochlorides, and in particular both in racemic and in non-racemic and in enantiomerically pure form. E-(4RS)-3-(4-Dimethylaminomethyl-3,4-dihydro-2H-benzo[b]oxepin-5-ylidenemethyl)-phenol in the form of its hydrocloride is particularly preferred.

The invention also provides a process for the preparation of the compounds of formula IA or IB according to the invention.

IA

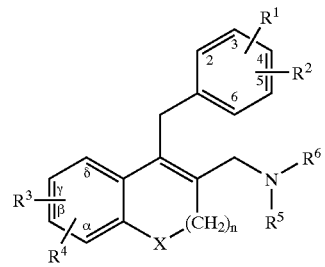

IB

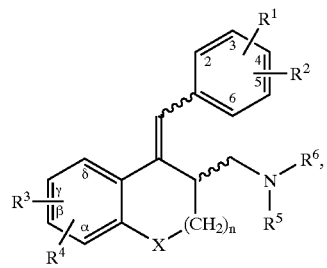

wherein
- R¹ denotes H, F, Cl, OH, O—CH₃, O—(C$_{2-6}$-alkyl), O—(C$_{3-7}$-cycloalkyl), CH₃, C$_{2-6}$-alkyl, CH₂F, CHF₂ or CF₃, in each case in the 2-, 3-, 4-, 5- or 6-position of the phenyl ring,
- R² denotes H, F, Cl, CH₃, C$_{2-6}$-alkyl, CH₂F, CHF₂ or CF₃, in each case in the 2-, 3-, 4-, 5- or 6-position of the phenyl ring,
- R³ and R⁴ independently of one another denote H, F, Cl, OH, O—CH₃, O—(C$_{2-6}$-alkyl), O—(C$_{3-7}$-cycloalkyl), CH₃, C$_{2-6}$-alkyl, CH₂F, CHF₂, CF₃, O-aryl, aryl or heterocyclyl, in each case in the α-, β-, γ- and/or δ-position of the aromatic ring,
- R⁵ and R⁶ independently of one another denote CH₃, C$_{2-6}$-alkyl, C$_{3-7}$-cycloalkyl, CH₂—(C$_{3-7}$-cycloalkyl), aryl, (C$_{1-6}$-alkyl)-aryl, heterocyclyl or (C$_{1-6}$-alkyl)-heterocyclyl,
- X denotes CH₂, O, S, SO or SO₂,
- n is 0, 1, 2 or 3 if X denotes CH₂, and is 1, 2 or 3 if X denotes O, S, SO or SO₂,
- and the configuration of the exocyclic double bond in compounds of formula IB is E or Z, wherein the process according to the invention is characterized by a process step (a) which comprises the reaction of a tertiary alcohol of formula II

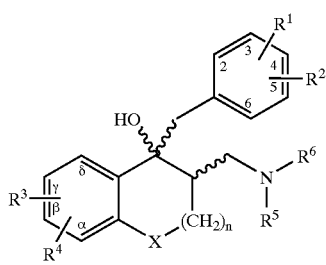

wherein R¹ to R⁶, X and n are as defined above, with an acid.

The use of half-concentrated or concentrated organic or inorganic acids is preferred here, in particular hydrochloric acid (HCl), e.g. 6N hydrochloric acid, optionally in an aqueous or an organic solvent, such as diethyl ether, concentrated hydrobromic acid (HBr), hydrogen bromide in glacial acetic acid (HBr/HOAc), e.g. a 33% hydrogen bromide solution in glacial acetic acid, methanesulfonic acid, methanesulfonic acid with methionine and formic acid.

Process step (a) is conventionally carried out at a temperature of about 0° C. to about 120° C.

By choice of a suitable acid, the preferred formation either of the endo isomer of the formula IA or of the exo isomer(s) of the formula IB can be achieved. The use of HBr in glacial acetic acid as the acid in process step (a) thus preferentially forms the endo compound IA, while, for example, the exo products IB are predominantly formed if 6N HCl is employed.

The compounds of formulae IA and IB formed by the process according to the invention and present in a mixture after carrying out process (a) can be separated from one another by means of conventional separation methods. It is also possible to achieve separation of the particular exo-E isomer of the formula IB from the corresponding exo-Z isomer of the formula IB. Suitable methods which may be mentioned by way of example are chromatographic separation processes, in particular liquid chromatography processes under normal pressure or increased pressure, preferably MPLC and HPLC processes, and crystallization processes. The enantiomers and/or diastereomers of the compounds IA and IB according to the invention formed can moreover be separated from one another with the aid of these and further processes known in the art, e.g. HPLC on chiral phases or fractional crystallization of diastereomeric salts formed with optically acid acids, such as (+)-tartaric acid, (−)-tartaric acid or (+)-10-camphorsulfonic acid.

Determination and assignment of the stereochemistry of the products prepared according to the invention, i.e. identification of the particular endo and exo double bond isomers and of the E and Z isomers, takes place with the aid of methods known in the prior art, for example by means of nuclear magnetic resonance spectroscopy (NMR) processes which are well-known in the prior art. Thus e.g. the exo isomers of the formula IB are differentiated from the endo isomers of the formula IA with the aid of the chemical shift of the benzylic hydrogen atom(s) in the ¹H-NMR spectrum. On the other hand, assignment of E/Z isomerism is possible via the different chemical shift of the phenyl ring protons in the ¹H-NMR spectrum due to anisotropy effects.

A preferred embodiment of the process according to the invention is characterized in that process step (a) comprises conversion of a tertiary alcohol of formula II in which at least one of the radicals R¹, R³ and R⁴ denotes O—CH₃ into compounds of formula IA or IB in which the radicals R¹, R³ and R⁴ denote OH, when the corresponding radicals R¹, R³ and R⁴ in the tertiary alcohol of formula II denote O—CH₃, with a reagent from the group which comprises hydrogen bromide in glacial acetic acid, concentrated hydrobromic acid and methanesulfonic acid/methionine. The process step is preferably carried out at a temperature of between 0° C. and 120° C., in particular at a temperature of between 20° C. and 50° C.

Another preferred embodiment of the process according to the invention is characterized in that, before process step (a), a process step (b) is carried out, which comprises conversion of a tertiary alcohol of formula III

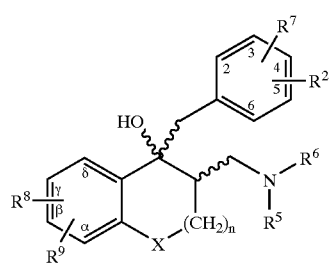

wherein
- R², R⁵, R⁶, X and n are as defined above,
- R⁷ denotes H, F, Cl, O—CH₃, O—(C$_{2-6}$-alkyl), O—(C$_{3-7}$-cycloalkyl), O—CH₂-phenyl, O—SiR¹⁰R¹¹R¹², wherein R¹⁰, R¹¹ and R¹² independently of one another are CH₃, C$_{2-6}$-alkyl or phenyl, CH₂F, CHF₂ or CF₃, in each case in the 2-, 3-, 4-, 5- or 6-position of the phenyl ring,
- R⁸ and R⁹ independently of one another denote H, F, Cl, O—CH₃, O—(C$_{2-6}$-alkyl), O—(C$_{3-7}$-cycloalkyl), O—CH₂-phenyl, O—SiR¹⁰R¹¹R¹², wherein R¹⁰, R¹¹ and R¹² independently of one another are CH₃, C$_{2-6}$-alkyl or phenyl, CH₂F, CHF₂, CF₃, O-aryl, aryl or heterocyclyl, in each case in the α-, β-, γ- and/or δ-position of the aromatic ring, and at least one of the radicals $R^7$, $R^8$ and $R^9$ is O—$CH_3$, O—($C_{2-6}$-alkyl), O—($C_{3-7}$-cycloalkyl), O—$CH_2$-phenyl or O—$SiR^{10}R^{11}R^{12}$, into a tertiary alcohol of formula II in which $R^1$, $R^3$ and $R^4$ are in each case OH, when the corresponding radical $R^7$, $R^8$ or $R^9$ in the formula III is O—$CH_3$, O—($C_{2-6}$-alkyl), O—($C_{3-7}$-cycloalkyl), O—$CH_2$-phenyl or O—$SiR^{10}R^{11}R^{12}$. If at least one of the radicals $R^7$, $R^8$ and $R^9$ represents a silanyloxy group (=O—$SiR^{10}R^{11}R^{12}$), O—$SiR^{10}R^{11}R^{12}$ preferably represents a trimethylsilyloxy, tert-butyldiphenylsilyloxy or tert-butyldimethylsilyloxy group.

If one or more of $R^7$, $R^8$ and $R^9$ represent a benzyloxy group (=O—$CH_2$-phenyl), process step (b) expediently comprises reductive debenzylation with catalytically activated hydrogen. Platinum or palladium, inter alia, can be used as the catalyst here, it being possible for the transition metal to be absorbed on a suitable support material, such as active charcoal. The reaction is preferably carried out in an organic solvent, e.g. acetic acid, methanol, ethanol, 2-propanol, 1-propanol, 1-butanol, 2-butanol or tert-butanol, under pressures of 1 bar ($10^5$ Pa) to 100 bar ($10^7$ Pa) and at temperatures of about 20° C. to about 100° C. The tertiary alcohols of formula III are preferably employed here in the form of one of their salts.

On the other hand, if one or more of $R^7$, $R^8$ and $R^9$ represent a silanyloxy group, process step (b) is preferably carried out either by treatment of the tertiary alcohol III with a fluoride anion, in particular tetra-n-butylammonium fluoride, in an inert solvent, such as e.g. tetrahydrofuran (THF), 1,4-dioxane or diethyl ether, preferably at room temperature, or by the action of methanolic hydrochloric acid.

If one or more of $R^7$, $R^8$ and $R^9$ in the tertiary alcohol of formula III represent methoxy (O—$CH_3$), O—($C_{2-6}$-alkyl) or O—($C_{3-7}$-cycloalkyl), process step (b) can be carried out by reaction of the compound III with diisobutylaluminium hydride in an aromatic hydrocarbon, such as toluene, preferably at a temperature of between about 60° C. and 130° C.

The new tertiary alcohols of formulae II and III which can be used for preparation of the cyclic substituted aminomethyl compounds of formulae IA and IB according to the invention form part of the present invention and can be obtained as intermediate compounds in a further process step (c), which is explained below, and then either purified and isolated by known methods or converted directly into the compounds of the formulae IA and/or IB by carrying out process steps (a) or (a) and (b) described above.

The tertiary alcohols II and III are preferably obtained here via a process step (c) which comprises reaction of a ketone of formula IV

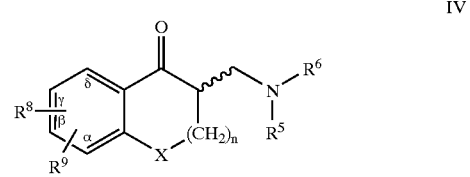

IV wherein $R^5$, $R^6$, $R^8$ and $R^9$, X and n are as defined above, with an organometallic compound of formula V

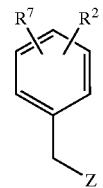

V wherein $R^2$ and $R^7$ are as defined above and Z denotes MgCl, MgBr, MgI or Li.

Process step (c) is suitably carried out in an ether solvent, preferably an aliphatic or cycloaliphatic ether, such as e.g. diethyl ether or THF, at a temperature of, in particular, between −70° C. and +60° C.

The ketones of formula IV employed in process step (c) are obtainable as Mannich bases, for example by a general process which is known e.g. from DE 197 55 480 A1 and DE 198 05 370 A1 and described inter alia by P. Horstmann and B. Unterhalt, *Arch. Pharm. Med. chem.* 330, 362–364 (1997) all of which are incorporated herein by reference in their entirety, from the corresponding ketone VI, formaldehyde and the amine VII (see equation 1):

equation 1

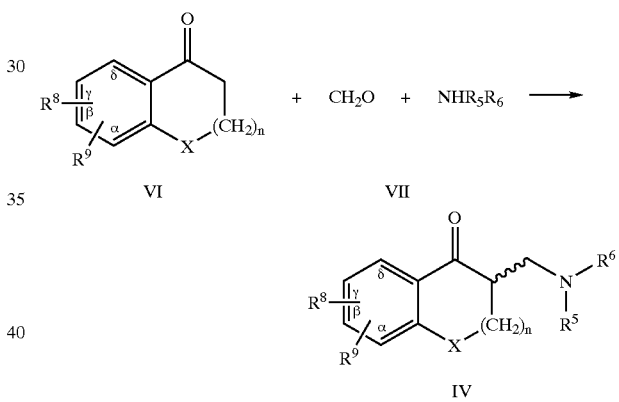

In the compounds of formulae IV, VI and VII, $R^5$, $R^6$, $R^8$, $R^9$ X and n are as defined above. The compounds of the formula VI, are commercially obtainable, or are otbainable, for example, from the corresponding carboxylic acids of formula VIII by intramolecular Friedel-Crafts acylation by means of a Lewis acid or a proton acid, such as e.g. polyphosphoric acid (see e.g. J. March: Advanced Organic Chemistry, 3rd ed., John Wiley & Sons, New York, Chichester, Brisbane, Toronto, Singapore (1985), pages 484 to 487, incorporated herein by reference):

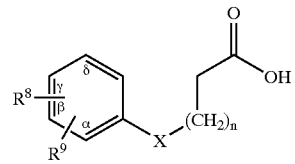

VIII

The organometallic compounds of formula V where Z=MgCl, MgBr, MgI or Li, are commercially available, or may be prepared, for example, by generally known processes by reaction of the corresponding chlorides, bromides or iodides, i.e. compounds of the formula V where Z=Cl, Br or I, with magnesium in an inert solvent by the Grignard method or with an organolithium reagent, e.g. n-butyllithium in n-hexane. The corresponding chlorides, bromides and iodides of formula V where Z=Cl, Br and I are in their turn either commercially available or obtainable e.g. by reaction of the corresponding benzyl alcohols of the formula V where Z=OH with suitable chlorinating, brominating or iodinating reagents (see, for example, J. March: Advanced Organic Chemistry, 3rd ed., John Wiley & Sons, New York, Chichester, Brisbane, Toronto, Singapore (1985), pages 382 to 384, incorporated herein by reference).

Where $R^7$, $R^8$ and/or $R^9$ in the compounds of formulae IV, V, VI and VIII denote O—$CH_3$, O—($C_{2-6}$-alkyl), O—($C_{3-7}$-cycloalkyl), O—$CH_2$-phenyl or O—$SiR^{10}R^{11}R^{12}$, these alkoxy, benzyloxy and silanyloxy compounds can be obtained from the corresponding hydroxy compounds, i.e. those compounds of the general formulae IV, V, VI and VIII in which one or more of $R^7$, $R^8$ and $R^9$ represent OH, by introduction of suitable protective groups by generally known processes, such as are described, for example, in T. W. Greene, P. G. M. Wuts: Protective Groups in Organic Synthesis, 1st ed., John Wiley & Sons, New York, Chichester, Brisbane, Toronto, Singapore (1991), which is incorporated herein by reference in its entirety.

Another preferred embodiment of the process according to the invention comprises a process step (d) in which compounds of formula IA or IB in which X denotes S and $R^1$ to $R^6$ and n are as defined above are converted into the corresponding compounds IA and/or IB where X=SO and/or $SO_2$ using an oxidizing agent. The oxidation of the sulfide (X=S) of formula IA or IB to the corresponding sulfoxide (X=SO) can be carried out, inter alia, with one equivalent of hydrogen peroxide (30 wt. % solution in water) in a suitable solvent, e.g. acetic acid, at a temperature of between about 20° C. and 60° C., and the oxidation to the sulfone (X=$SO_2$) can be carried out with a further equivalent of hydrogen peroxide. Further suitable oxidizing agents are, inter alia, sodium perborate, t-butyl hypochlorite, sodium periodate and potassium hydrogen persulfate (Oxone®) (see also J. March: Advanced Organic Chemistry, 3rd ed., John Wiley & Sons, New York, Chichester, Brisbane, Toronto, Singapore (1985), pages 1089 and 1090).

It is furthermore preferable, for conversion of compounds of formula IA or IB in which at least one of the radicals $R^1$, $R^3$ and $R^4$ denotes O—$CH_3$ into compounds of formula IA or IB in which the corresponding radicals $R^1$, $R^3$ and $R^4$ denotes OH, to carry out a process step (e) after process step (a) and optionally before or after process step (d). This process step (e) can be carried out e.g. using diisobutylaluminium hydride in an aromatic hydrocarbon, such as e.g. toluene or xylene, at a temperature of 60° C. to 130° C. An alternative procedure for step (e) comprises reaction with methanesulfonic acid/methionine at a temperature of 20° C. to 50° C.

It is moreover preferred to carry out, after process step (a) or (d) or (e), a process step (f) which comprises conversion of the compounds IA and/or IB according to the invention into their pharmaceutically acceptable salts. Process step (f) is preferably carried out by reaction of the compounds IA and/or IB, in the liquid or solid phase, with inorganic or organic acids—which can optionally also be bonded to a solid phase—such as, preferably, hydrochloric acid, hydrobromic acid, sulfuric acid, phosphoric acid, carbonic acid, p-toluenesulfonic acid, methanesulfonic acid, formic acid, acetic acid, oxalic acid, succinic acid, tartaric acid, mandelic acid, fumaric acid, lactic acid, citric acid, glutamic acid or aspartic acid, which form physiologically tolerated and therefore pharmaceutically acceptable salts with the compounds IA and/or IB according to the invention. The salts formed are, inter alia, hydrochlorides, hydrobromides, phosphates, carbonates, bicarbonates, formates, acetates, oxalates, succinates, tartrates, fumarates, citrates and glutamates. The salt formation is preferably carried out in an organic solvent, such as diethyl ether, diisopropyl ether, alkyl acetates, acetone or methyl ethyl ketone. The particularly preferred hydrochlorides of the compounds according to the invention are accessible, in particular, by carrying out process step (f) with trimethylchlorosilane in an aqueous organic solvent. The hydrates, such as mono-, sesqui-, di-, tri- and tetrahydrates, are furthermore preferred salts of the compounds according to the invention which can be obtained, for example by crystallization from aqueous solution.

In another preferred process step (g), which can be carried out after process step (a) or before or after process step (d) or before or after process step (e) or after process step (f), the compounds of the general formulae IA and IB or their pharmaceutically acceptable salts are separated from one another. The separation can be carried out by means of known separation processes, it also being possible to achieve separation of the particular exo-E isomer of the formula IB from the corresponding exo-Z isomer of the formula IB. Suitable methods are chromatographic separation processes, in particular liquid chromatography processes under normal or increased pressure, preferably MPLC and HPLC processes, and processes of fractional crystallization. The enantiomers and/or diastereomers of the compounds IA and IB according to the invention formed can moreover be separated from one another with the aid of these and further processes known to those ordinarily skilled in the art, e.g. HPLC on chiral phases or fractional crystallization of diastereomeric salts formed with chiral acids, such as (+)-tartaric acid, (−)-tartaric acid or (+)-10-camphorsulfonic acid.

The invention furthermore provides a medicament which comprises at least one of the cyclic substituted aminomethyl compounds of formula IA or IB according to the invention and their pharmaceutically acceptable salts. The compounds according to the invention may be present here in the medicament according to the invention as isomerically pure, in particular enantiomerically pure or diastereomerically pure, compounds, but may also be as a racemic or non-racemic mixture. It is preferable here for the medicament to comprise a pharmaceutically acceptable salt of the compounds according to the invention, in particular a hydrochloride.

The invention also provides the use of at least one cyclic substituted aminomethyl compound of formula IA or IB according to the invention, including their diastereomers or enantiomers, also as racemates or an enantiomer mixture in the form of their free base or of a salt formed with a physiologically tolerated acid, in particular the hydrochloride salt, for the preparation of a medicament for treatment of pain. Also provided is a method for treating pain using the pharmaceutical administering to a patient in need thereof an effective pain-treating amount of the above pharmaceutical composition.

The compounds according to the invention have proved to have an analgesic action in vivo. At the same time, the compounds according to the invention do not bind or scarcely bind to $\mu$-receptors and have no specific activity on $\delta$-receptors. It is thus found in the $\mu$-opiate receptor binding test according to P. L. Wood (P. L. Wood et al.,

*Neuropharmacology*, vol. 20, 1215 et seq. (1981)) that the compounds of the general formulae IA and IB according to the invention do not bind (0–20% inhibition at a concentration of 1 μM) or bind only very weakly ($K_i$>1 μM) to the μ-receptor. In the δ-opiate receptor binding test according to L. K. Vaughn (L. K. Vaughn et al. *Eur. J. Pharmacol.*, vol. 177, 99 et seq. (1990)), the compounds according to the invention show no specific activity on the δ-receptor (0–30% inhibition at a concentration of 1 μM; $K_i$>1 μM).

Surprisingly, it has been found that the cyclic substituted aminomethyl compounds of formula IA or IB according to the invention are very suitable for further indications, in particular for treatment of urinary incontinence, itching, tinnitus aurium and/or diarrhea. The Application therefore also provides the use of at least one cyclic substituted aminomethyl compound of formula IA or IB according to the invention, including a pharmaceutically acceptable salt, for the preparation of a medicament for treatment of urinary incontinence, itching tinnitus aurium and/or diarrhea.

The present invention furthermore provides pharmaceutical compositions which comprise at least one compound of formula IA or IB as defined above or one of its pharmaceutically acceptable salts and one or more pharmaceutical auxiliary substances.

The medicaments and pharmaceutical compositions according to the invention can be present and administered as liquid, semi-solid or solid medicament forms and in the form of injection solutions, drops, juices, syrups, suspensions, sprays, granules, tablets, pellets, patches, capsules, plasters, suppositories, ointments, creams, lotions, gels, emulsions or aerosols, and comprise, in addition to at least one cyclic substituted aminomethyl compound of formula IA or IB according to the invention, pharmaceutical auxiliary substances according to the galenical form, such as carrier materials, fillers, solvents, diluents, surface-active substances, dyestuffs, preservatives, disintegrating agents, anti-friction agents, lubricants, flavourings and/or binders. These auxiliary substances can be, for example: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatine, sorbitol, inositol, mannitol, microcrystalline cellulose, methylcellulose, carboxymethylcellulose, cellulose acetate, shellac, cetyl alcohol, polyvinylpyrrolidone, paraffins, waxes, naturally occurring and synthetic gums, acacia gum, alginates, dextran, saturated and unsaturated fatty acids, stearic acid, magnesium stearate, zinc stearate, glyceryl stearate, sodium lauryl sulfate, edible oils, sesame oil, coconut oil, ground nut oil, soya bean oil, lecithin, sodium lactate, polyoxyethylene and -propylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc, kaolin, pectin, crosspovidone, agar and bentonite. The choice of auxiliary materials and the amounts thereof to be employed depend on whether the medicament is to be administered orally, perorally, subcutaneously, parenterally, intravenously, intraperitoneally, intradermally, intramuscularly, intranasally, buccally, rectally or locally, for example to infections on the skin, the mucous membranes and the eyes. Formulations in the form of tablets, coated tablets, capsules, granules, drops, juices and syrups are suitable, inter alia, for oral administration, and solutions, suspensions, easily reconstitutable dry formulations and sprays are suitable for parenteral, topical and inhalatory administration. Cyclic substituted aminomethyl compounds of formula IA or IB according to the invention in a depot in dissolved form or in a patch, optionally with the addition of agents which promote penetration through the skin, are suitable formulations for percutaneous administration. Formulation forms which can be used orally or percutaneously can release the cyclic substituted aminomethyl compounds of formula IA or IB according to the invention in a delayed manner.

The medicaments and pharmaceutical compositions according to the invention are prepared with the aid of agents, devices, methods and processes which are well-known in the prior art of pharmaceutical formulation, such as are described, for example, in "Remington's Pharmaceutical Sciences", ed. A. R. Gennaro, 17th ed., Mack Publishing Company, Easton, Pa. (1985), in particular in part 8, sections 76 to 93.

Thus, for a solid formulation, such as a tablet, the active compound of the medicament, i.e. a compound of formula IA or IB or one of its pharmaceutically acceptable salts, can be mixed with a pharmaceutical carrier, e.g. conventional tablet constituents, such as maize starch, lactose, sucrose, sorbitol, talc, magnesium stearate, dicalcium phosphate or gum, and pharmaceutical diluents, such as water, in order to form a solid preformulation composition which comprises a compound according to the invention or a pharmaceutically acceptable salt thereof in homogeneous distribution. Homogeneous distribution here is understood as meaning that the active compound is distributed uniformly over the entire preformulation composition, so that this can easily be divided into unit dose forms of the same action, such as tablets, pills or capsules. The solid preformulation composition is then divided into unit dose forms. The tablets or pills of the medicament according to the invention or of the compositions according to the invention can also be coated, or compounded in another manner in order to provide a dose form with delayed release. Suitable coating compositions are, inter alia, polymeric acids and mixtures of polymeric acids with materials such as shellac, cetyl alcohol and/or cellulose acetate.

The amount of active compound to be administered to the patient varies and depends on the weight, age and disease history of the patient, as well as on the mode of administration, the indication and the severity of the disease. 0.1 to 5,000 mg/kg, in particular 1 to 500 mg/kg, preferably 2 to 250 mg/kg of body weight of at least one cyclic substituted aminomethyl compound of formula IA or IB according to the invention are usually administered.

EXAMPLES

The following examples serve to illustrate the present invention in more detail.

Silica gel 60 (0.040–0.063 mm) from E. Merck, Darmstadt was employed as the stationary phase for the column chromatography.

The thin layer chromatography analyses were carried out with HPTLC precoated plates, silica gel 60 F 254, from E. Merck, Darmstadt.

The mixture ratios of the mobile phases for all the chromatography analyses and separations are always stated in volume/volume.

The Mannich bases of the general formula IV were synthesized by the method described by P. Horstmann and B. Unterhalt, *Arch. Pharm. Med. Chem.* 330, 362–364

(1997), and in the patent applications DE 198 05 370 A1 and DE 197 55 480 A1.

$^1$H-NMR analyses to determine the stereochemistry (exo/endo double bond or E/Z configuration) of the inventions [sic] according to the invention were carried out with a 300 MHz DPX Advance NMR apparatus from Bruker.

Example 1

[1-(3-Methoxybenzyl)-3,4-dihydro-naphth-2-ylmethyl]-dimethylamine hydrochloride

1st Stage:

(1RS,2RS)-2-Dimethylaminomethyl-1-(3-methoxybenzyl)-1,2,3,4-tetrahydro-naphth-1-ol A solution of 8.13 g 2-dimethylaminomethyl-3,4-dihydro-naphthalen-1-one in 20 ml dry diethyl ether was added dropwise to a freshly prepared Grignard reagent of 1.46 g magnesium filings and 8.8 ml 3-methoxybenzyl chloride in 50 ml dry diethyl ether at 20° C., while stirring. The reaction mixture was heated under reflux for 3 hours, decomposed by dropwise addition of 30 ml of a saturated ammonium chloride solution and, after dilution with distilled water, extracted three times with 50 ml diethyl ether each time. The extracts were washed with a saturated sodium chloride solution, dried over sodium sulfate and evaporated in vacuo. The oily residue was purified by column chromatography with ethyl acetate/methanol=20/1 as the eluting agent. 9.41 g (72.3% of th.) of the title compound were obtained here as a diastereomer mixture.

2nd Stage:

[1-(3-Methoxybenzyl)-3,4-dihydro-naphth-2-ylmethyl]-dimethylamine hydrochloride 6.51 g of the product from stage 1 were stirred with 75 ml of a solution of hydrogen bromide in glacial acetic acid (33% HBr) at 60° C. for one hour. The mixture was then evaporated in vacuo and the residue was taken up in 150 ml water. The mixture was rendered alkaline with potassium carbonate and extracted three times with 50 ml methylene chloride each time. The extracts were washed with a saturated sodium chloride solution, dried over sodium sulfate and evaporated in vacuo. The crude base of the title compound obtained in this manner was converted into the hydrochloride with trimethylchlorosilane/water in 2-butanone.

| Yield: | 5.81 g (84.5% of th.) |
|---|---|
| Melting point: | 202–204° C. |

Example 2

[1-(4-Chlorobenzyl-3,4-dihydro-naphth-2-ylmethyl]-dimethylamine hydrochloride

The title compound was obtained using the procedure described in example 1, employing 4-chlorobenzyl chloride instead of the 3-methoxy compound in stage 1.

Melting point: 247–248° C.

Example 3

3-(2-Dimethylaminomethyl-3,4-dihydro-naphth-1-ylmethyl)-phenol hydrochloride

A: 4.71 g of the product from example 1, stage 1 were heated under reflux in 60 ml of a solution of hydrogen bromide in glacial acetic acid for 5 hours. The mixture was then evaporated in vacuo, the residue was taken up in 50 ml water and the mixture was neutralized by addition of 1 N sodium hydroxide solution and finally rendered alkaline with ammonium hydroxide. It was extracted three times with 30 ml ethyl acetate each time and the extracts were dried over sodium sulfate and evaporated in vacuo. The crude base of the title compound which remained was converted into the hydrochloride with trimethylchlorosilane/water in 2-butanone.

| Yield: | 3.75 g (78.4% of th.) |
|---|---|
| Melting point: | 151–153° C. (decomp.) |

The title compound may also be obtained by the following route:

B: 40 ml of a solution of diisobutylaluminium hydride in toluene (20 wt. %) were added to a suspension of 2.06 g of the product from example 1 in 20 ml dry toluene and the mixture was heated under reflux for 12 hours. After cooling, decomposition was carried out by dropwise addition of ethanol, finally mixed with water, and the mixture was evaporated in vacuo. 30 ml methanol were added to the residue and the mixture was filtered over filtering earth. The filtrate was evaporated and the crude base of the title compound obtained in this manner was converted with trimethylchlorosilane/water in 2-butanone into the hydrochloride, the melting properties of which were identical to those of the product obtained above.

Yield: 1.58 g (79.6% of th.)

Example 4

Using the procedure described in example 3, method A and employing corresponding tertiary alcohols, the following were obtained analogously:

4a: 5-(4-Chlorobenzyl)-6-dimethylaminomethyl-7,8-dihydro-naphth-2-ol hydrochloride
  Melting point: 110° C. (decomp.)
4b: [1-(2,4-Dichlorobenzyl)-3,4-dihydro-naphth-2-ylmethyl]-dimethyl-amine hydrochloride
  Melting point: 208–209° C.
4c: 5-(4-Chlorobenzyl)-6-dimethylaminomethyl-7,8-dihydro-naphth-1-ol hydrochloride
  Melting point: 136–139° C.
4d: [5-(4-Chlorobenzyl)-8,9-dihydro-7H-benzocyclohepten-6-ylmethyl]-dimethylamine hydrochloride
  Melting point: 240–243° C.
4e: E-(5RS)-[5-(4-Chlorobenzylidene)-6,7,8,9-tetrahydro-5H-benzocyclohepten-6-ylmethyl]-dimethylamine hydrochloride
  Melting point: 181–183° C.

As products of the same batch, the example compounds 4d and 4e were separated in the form of the free bases by column chromatography with ethyl acetate/methanol (9/1) as the eluting agent.

4f: 6-Dimethylaminomethyl-5-(3-hydroxybenzyl)-7,8-dihydro-naphth-2-ol hydrochloride
  Melting point: 89° C. (decomp.)

Example 5

[1-(2-Methoxybenzyl)-3,4-dihydro-naphth-2-ylmethyl]-dimethylamine hydrochloride (5a)

and

E-(2RS)-[1-(2-Methoxybenzylidene)-1,2,3,4-tetrahydro-naphth-2-ylmethyl]-dimethylamine hydrochloride (5b)

A solution of 7.06 g (1RS,2RS)-2-dimethylaminomethyl-1-(2-methoxy-benzyl)-1,2,3,4-tetrahydronaphth-1-ol (prepared analogously to example 1, stage 1 from 2-methoxybenzyl chloride and 2-dimethylaminomethyl-3,4-dihydronaphthalen-1-one) in 45 ml formic acid was stirred at 20° C. for 3 hours. It was diluted with 100 ml water and rendered alkaline by addition of potassium carbonate in portions up to pH 9. The mixture was extracted three times with 50 ml methylene chloride each time. The extracts were washed with saturated sodium chloride solution, dried over sodium sulfate and evaporated in vacuo. The residue was separated by column chromatography with ethyl acetate as the eluting agent, the two title compounds being obtained as bases, which were converted into the hydrochlorides with trimethylchlorosilane/water in 2-butanone.

| 5a: | Yield: | 3.12 g (51.5% of th.) |
|---|---|---|
| | Melting point: | 181–183° C. |
| 5b: | Yield: | 2.38 g (39.3% of th.) |
| | Melting point: | 228–230° C. |

Example 6

3-(4-Dimethylaminomethyl-2,3-dihydro-benzo[b]oxepin-5-ylmethyl)-phenol hydrochloride (6a), E-(4RS)3-(4-Dimethylaminomethyl-3,4-dihydro-2H-benzo[b]oxepin-5-ylidene-methyl)-phenol hydrochloride (6b)

and

Z-(4RS)3-(4-Dimethylaminomethyl-3,4-dihydro-2H-benzo[b]oxepin-5-ylidene-methyl)-phenol hydrochloride (6c)

A mixture of 4.78 g (4RS,5RS)-4-dimethylaminomethyl-5-(3-methoxybenzyl)-2,3,4,5-tetrahydrobenzo[b]oxepin-5-ol (prepared from 3-methoxybenzylmagnesium chloride and 4-dimethylaminomethyl-3,4-dihydro-2H-benzo[b]oxepin-5-one analogously to example 1, stage 1), 28 ml methanesulfonic acid and 3.20 g methionine was stirred at 40° C. for 4 days. Ice was then added and the mixture was cautiously rendered alkaline with sodium bicarbonate. It was extracted three times with 30 ml ethyl acetate each time and the extracts were washed with a saturated sodium chloride solution, dried over sodium sulfate and evaporated in vacuo. The crude product mixture obtained in this manner was separated by column chromatography with ethyl acetate and the individual compounds were converted into their hydrochlorides with trimethylchlorosilane/water in 2-butanone.

| 6a: | Yield: | 0.88 g (18.1% of th.) |
|---|---|---|
| | Melting point: | 194–196° C. |
| 6b: | Yield: | 0.76 g (15.7% of th.) |
| | Melting point: | 120° C. (decomp.) |
| 6c: | Yield: | 1.29 g (26.5% of th.) |
| | Melting point: | 154° C. (decomp.) |

Example 7

[5-(4-Chlorobenzyl)-2,3-dihydro-benzo[b]-oxepin-4-ylmethyl]-dimethylamine hydrochloride (7a), E-(4RS)[5-(4-Chlorobenzylidene)-2,3,4,5-tetrahydro-benzo[b]oxepin-4-yl-methyl]-dimethylamine hydrochloride (7b)

and

Z-(4RS) [5-(4-Chlorobenzylidene)-2,3,4,5-tetrahydro-benzo[b]oxepin-4-yl-methyl]-dimethylamine hydrochloride (7c)

7.27 g (4RS,5RS)-5-(4-chlorobenzyl)-4-dimethylamino-methyl-2,3,4,5-tetrahydrobenzo[b]oxepin-5-ol were reacted with 43 ml methanesulfonic acid and 4.81 g methionine analogously to the procedure described in example 6. After similarly analogous working up, separation of the product and salt formation, the title compounds were obtained in the form of white crystals.

| 7a: | Yield: | 3.07 g(40.1% of th.) |
|---|---|---|
| | Melting point: | 215–217° C. |
| 7b: | Yield: | 0.93 g (12.1% of th.) |
| | Melting point: | 92° C. (decomp.) |
| 7c: | Yield: | 1.69 g (22.1% of th.) |
| | Melting point: | 162–164° C. |

Example 8

2-Chloro-5-(4-dimethylaminomethyl-2,3-dihydro-benzo[b]oxepin-5-ylmethyl)-phenol hydrochloride 0.80 g (42.7% of th.) of the title compound were obtained from 1.85 g (4RS,5RS)-5-(4-chloro-3-methoxybenzyl)-4-dimethylaminomethyl-2,3,4,5-tetrahydro-benzo[b]oxepin-5-ol, 10 ml methanesulfonic acid and 1.12 g methionine using the procedure described in example 6.

Melting point: 220–222° C.

Example 9

3-(4-Dimethylaminomethyl-2, 3-dihydro-benzo[b]thiepin-5-ylmethyl)-phenol hydrochloride (9a)

and

Z-(4RS)-3-(4-Dimethylaminomethyl-3,4-dihydro-2H-benzo[b]thiepin-5-ylidenemethyl)-phenol hydrochloride (9b)

The title compounds were obtained from 8.00 g (4RS,5RS)-4-dimethylaminomethyl-5-(3-methoxybenzyl)-2,3,4,5-tetrahydro-benzo[b]thiepin-5-ol, 45 ml methanesulfonic acid and 5.11 g methione using the procedure described in example 6, after separation of the products by column chromatography with ethyl acetate/methanol=3/1 as the eluting agent and conversion into the hydrochlorides.

| 9a: | Yield: | 3.43 g (42.2% of th.) |
|---|---|---|
|  | Melting point: | 92% (decomp.) |
| 9b: | Yield: | 1.57 g (19.4% of th.) |
|  | Melting point: | 209–210° C. |

Example 10

(1RS)-3-(4-Dimethylaminomethyl-1-oxo-2,3-dihydro-benzo[b]thiepin-5-yl-methyl)-phenol hydrochloride 0.60 g of the product from example 9a in 6 ml acetic acid and 0.5 ml of an aqueous solution of hydrogen peroxide (30 wt. % $H_2O_2$) were stirred at 20° C. for 2 hours. The mixture was diluted with 30 ml water and rendered alkaline first with 3N sodium hydroxide solution and then with potassium carbonate to a pH of 8. The mixture was extracted three times with 20 ml ethyl acetate each time. The combined extracts were washed with saturated sodium chloride solution, dried over sodium sulfate and evaporated in vacuo. The residue was converted into the hydrochloride with trimethylchlorosilane/water in 2-butanone. 0.53 g (84.5% of th.) of the title compound was obtained in this manner.

Melting point: 96° C. (decomp.)

Example 11

[5-(4-Chlorobenzyl)-2,3-dihydro-benzo[b]thiepin-4-ylmethyl]-dimethylamine hydrochloride 3.00 g (4RS,5RS)-5-(4-chlorobenzyl)-4-dimethylaminomethyl-2,3,4,5-tetrahydro-benzo[b]thiepin-5-ol (prepared as described in example 1, stage 1 from (4RS)-4-dimethylaminomethyl-3,4-dihydro-2H-benzo[b]thiepin-5-one and 4-chlorobenzylmagnesium chloride), 17 ml methanesulfonic acid and 1.90 g methionine were stirred at 50° C. for 7 days. After working up, purification and conversion into the hydrochloride, as described in example 6, 1.87 g (59.4% of th.) of the title compound were obtained.

Melting point: 223–224° C.

Example 12

(1R,S)-[5-(4-Chlorobenzyl)-1-oxo-2,3-dihydro-benzo[b]thiepin-4-ylmethyl]-dimethylamine hydrochloride 0.25 g of the product from example 11 was oxidized in 2.3 ml acetic acid with 0.2 ml of an aqueous solution of hydrogen peroxide (30 wt. % $H_2O_2$) using the procedure described in example 10. After processing and hydrochloride formation, 0.21 g (80.6% of th.) of the title compound was obtained.

Melting point: 227–229° C.

Example 13

E-(4RS)-[5-(3-Methoxybenzylidene)-2,3,4,5-tetrahydro-benzo[b]oxepin-4-ylmethyl]-dimethylamine hydrochloride 1.00 g (4RS,5RS)-4-dimethylaminomethyl-5-(3-methoxybenzyl)-2,3,4,5-tetrahydro-benzo[b]oxepin-5-ol (see example 6) and 48 ml 6N hydrocloric acid were stirred at 20° C. for 24 h and at 50° C. for 8 h. The mixture was then rendered alkaline with 6N sodium hydroxide solution and extracted three times with 20 ml ethyl acetate each time. The extracts were washed with a saturated sodium chloride solution, dried over sodium sulfate and evaporated in vacuo. The residue was purified by column chromatography with ethyl acetate as the eluting agent. After conversion into the hydrochloride with a solution of hydrogen chloride in diethyl ether, 0.72 g (68.6% of th.) of the title compound was obtained.

Melting point: 170–172° C.

Example 14

E-(4RS)-[5-(3-Methoxybenzylidene)-2,3,4,5-tetrahydro-benzo[b]thiepin-4-ylmethyl]-dimethylamine hydrochloride (14a) and its Z isomer (14b)

5.00 g (4RS,5RS)-4-dimethylaminomethyl-5-(3-methoxybenzyl)-2,3,4,5-tetrahydro-benzo[b]thiepin-5-ol (see example 9) were reacted with 230 ml 6N hydrochloric acid by the procedure described in example 13. After processing, separation of the double bond isomers by column chromatography with ethyl acetate/methanol=3/1 and conversion into the hydrochloride, the title compounds were obtained in the form of white crystals.

| 14a: | Yield: | 1.10 g (20.9% of th.) |
|---|---|---|
|  | Melting point: | 166–169° C. |
| 14b: | Yield: | 2.56 g (48.7% of th.) |
|  | Melting point: | 164–167° C. |

Pharmaceutical Formulation of a Medicament According to the Invention 1 g of the hydrochloride of compound 6b (E-(4RS)3-(4-dimethylaminomethyl-3,4-dihydro-2H-benzo[b]oxepin-5-ylidenemethyl)-phenol hydrochloride) was dissolved in 1 l water for injection purposes at room temperature and the solution was then adjusted to isotonic conditions by addition of NaCl (sodium chloride).

Pharmacological Investigation of the Compounds According to the Invention

The antinociceptive activity of the compounds according to the invention was investigated in mice in the phenylquinone-induced writhing test, modified by I. C. Hendershot, J. Forsaith, J. Pharmacol. Exp. Ther. 125, 237–240 (1959). Male NMRI mice weighing 25–30 g were employed for this. Groups of 10 animals per substance dose received 0.3 ml/mouse of a 0.02% aqueous solution of phenylquinone (phenylbenzoquinone, Sigma, Deisenhofen; preparation of the solution with the addition of 5% ethanol and storage in a water bath at 45° C.) administered intraperitoneally 10 minutes after intravenous administration of a compound according to the invention. The animals were placed individually in observation cages. The number of pain-induced stretching movements (so-called writhing reactions=straightening of the body with stretching of the hind extremities) was counted by means of a push-button counter for 5–20 minutes after the administration of phenylquinone.

The $ED_{50}$ values of the writhing reaction were calculated by means of regression analysis (evaluation program, Martens EDV Service, Eckental) from the dose-dependent decrease in writhing reactions compared with animal groups investigated in parallel to which no compound according to the invention was administered.

The majority of the substances were tested in the standard dose of 10 mg/kg. The percentage inhibition (% inhibition)

of the writhing reactions by a substance was then calculated according to the following equation:

$$\% \text{ inhibition} = 100 - \left( \frac{\text{writhing reaction in treatment animals}}{\text{writhing reaction in control animals}} \times 100 \right)$$

The results are summarized in table 1 for selected compounds.

TABLE 1

| Example no. | Writhing test, mouse, i.v. decrease in writhing reactions or $ED_{50}$ [mg/kg] |
|---|---|
| 2 | 6.85 (61.5%) |
| 3 | 93% |
| 4e | 69% |
| 4c | 84% |
| 7c | 79% |
| 6a | 95% |
| 6b | 91% [21.5 mg/kg] |
| 6c | 78% |

The results reproduced in table 1 show that the compounds according to the invention, in particular example compound no. 6b (E-(4RS)3-(4-dimethylaminomethyl-3,4-dihydro-2H-benzo[b]oxepin-5-ylidenemethyl)-phenol hydrochloride), which already causes 91% inhibition at a dose of 2.15 mg/kg body weight, have an analgesic action in vivo. At the same time the compounds according to the invention do not bind or scarcely bind to μ-receptors and have no specific activity on δ-receptors.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A cyclic substituted aminomethyl compound of formula IA or IB

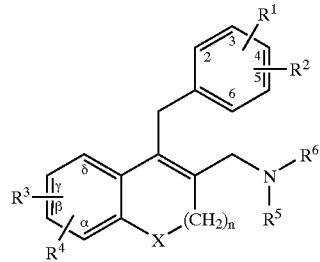

IA

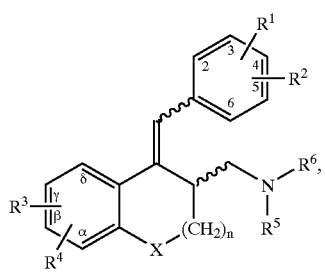

IB wherein
$R^1$ denotes H, F, Cl, OH, O—($C_{1-6}$-alkyl), O—($C_{3-7}$-cycloalkyl), $CH_3$, $C_{2-6}$-alkyl, $CH_2F$, $CHF_2$ or $CF_3$,
$R^2$ denotes H, F, Cl, $C_{1-6}$-alkyl, $CH_2F$, $CHF_2$ or $CF_3$,
$R^3$ and $R^4$ independently of one another denote H, F, Cl, OH, O—($C_{1-6}$-alkyl), O—($C_{3-7}$-cycloalkyl), $C_{1-6}$-alkyl, $CH_2F$, $CHF_2$, $CF_3$, O-aryl, aryl or heterocyclyl, $R^5$ and $R^6$ independently of one another denote $C^{1-6}$-alkyl, $C_{3-7}$-cycloalkyl, $CH_2$—($C_{3-7}$-cycloalkyl), aryl, ($C_{1-6}$-alkyl)-aryl, heterocyclyl or ($C_{1-6}$-alkyl)-heterocyclyl,
X denotes $CH_2$, O, S, SO or $SO_2$, and
n is 0, 1, 2 or 3 if X denotes $CH_2$, and is 1, 2 or 3 if X denotes O, S, SO or $SO_2$,
or a pharmaceutically acceptable salt thereof.

2. A cyclic substituted aminomethyl compound according to claim 1, wherein the configuration of the exocyclic double bond in a compound of formula IB is E.

3. A cyclic substituted aminomethyl compound according to claim 1, wherein the configuration of the exocyclic double bond in a compound of formula IB is Z.

4. A cyclic substituted aminomethyl compound according to claim 1, wherein the compound corresponds to formula IA, and wherein, independently of one another, $R^1$ denotes OH, O—$CH_3$ or Cl; $R^2$ denotes H or Cl; $R^3$ denotes H or Cl; $R^3$ denotes H or OH; $R^4$ denotes H; $R^5$ and $R^6$ denote $CH_3$; X denotes $CH_2$, O, S or SO; and n is 1 or 2,
or a pharmaceutically acceptable salt thereof.

5. A cyclic substituted aminomethyl compound according to claim 4, wherein, independently of one another, $R^1$ denotes 3-OH, 2-O—$CH_3$, 3-O—$CH_3$ or 4-Cl; $R^2$ denotes H, 2-Cl or 4-Cl; $R^3$ denotes H, α-OH or β-OH; $R^4$ denotes H, $R^5$ and $R^6$ denote $CH_3$; X denotes $CH_2$, O, S or SO; and n is 1 or 2,
or a pharmaceutically acceptable salt thereof.

6. A cyclic substituted aminomethyl compound according to claim 1, wherein the compound corresponds to formula IB, wherein $R^1$ denotes OH, O—$CH_3$ or Cl; $R^2$, $R^3$ and $R^4$ denote H; $R^5$ and $R^6$ denote $CH_3$; X denotes $CH_2$, O or S; and n is 1 or 2,
or a pharmaceutically acceptable salt thereof.

7. A cyclic substituted aminomethyl compound according to claim 6, wherein $R^1$ denotes 3-OH, 2-O—$CH_3$, 3-O—$CH_3$ or 4-Cl; $R^2$, $R^3$ and $R^4$ denote H; $R^5$ and $R^6$ denote $CH_3$; X denotes $CH_2$, O or S; and n is 1 or 2,
or a pharmaceutically acceptable salt thereof.

8. A cyclic substituted aminomethyl compound according to claim 1, wherein the compound is in the form of a mixture of the isomers with an endocyclic double bond according to formula IA, and with an exocyclic double bond according to formula IB.

9. A cyclic substituted aminomethyl compound according to claim 1, in the form of its racemate, or a pharmaceutically acceptable salt.

10. A cyclic substituted aminomethyl compound according to claim 1, in the form of a pure enantiomer, or in the form of mixtures of enantiomers in any desired mixture ratio, or their pharmaceutically acceptable salts.

11. A cyclic substituted aminomethyl compound according to claim 1, selected from the group consisting of:
[1-(4-chlorobenzyl)-3,4-dihydro-naphth-2-ylmethyl]-dimethylamine,
3-(2-dimethylaminomethyl-3,4-dihydro-naphth-1-yl-methyl)-phenol,
5-(4-chlorobenzyl)-6-dimethylaminomethyl-7,8-dihydro-naphth-1-ol,
E-(5RS)-[5-(4-chlorobenzylidene)-6,7,8,9-tetrahydro-5H-benzocyclohepten-6-ylmethyl]-dimethylamine,
Z-(4RS)-[5-(4-chlorobenzylidene)-2,3,4,5-tetrahydro-benzo[b]oxepin-4-ylmethyl]-dimethylamine,
3-(4-dimethylaminomethyl-2,3-dihydro-benzo[b]oxepin-5-ylmethyl)-phenol, E-(4RS)-3-(4-dimethylaminomethyl-3,4-dihydro-2H-benzo[b]oxepin-5-ylidenemethyl)-phenol, Z-(4RS)-3-(4-dimethylaminomethyl-3,4-dihydro-2H-benzo [b]oxepin-5-ylidenemethyl)-phenol, and their pharmaceutically acceptable salts.

12. A cyclic substituted aminomethyl compound according to claim 11, wherein the compound is a hydrochloride.

13. A process for the preparation of a compound of formula IA or IB

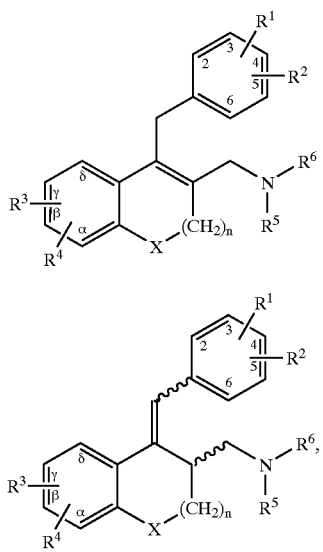

wherein $R^1$ denotes H, F, Cl, OH, O—($C_{1-6}$-alkyl), O—($C_{3-7}$-cycloalkyl), $C_{1-6}$-alkyl, $CH_2F$, $CHF_2$ or $CF_3$, $R^2$ denotes H, F, Cl, $C_{1-6}$-alkyl, $CH_2F$, $CHF_2$ or $CF_3$, $R^3$ and $R^4$ independently of one another denote H, F, Cl, OH, O—($C_{1-6}$-alkyl), O—($C_{3-7}$-cycloalkyl), $C_{1-6}$-alkyl, $CH_2F$, $CHF_2$, $CF_3$, O-aryl, aryl or heterocyclyl, $R^5$ and $R^6$ independently of one another denote $C_{1-6}$-alkyl, $C_{3-7}$-cycloalkyl, $CH_2$—($C_{3-7}$-cycloalkyl), aryl, ($C_{1-6}$-alkyl)-aryl, heterocyclyl or ($C_{1-6}$-alkyl)-heterocyclyl, X denotes $CH_2$, O, S, SO or $SO_2$, and n is 0, 1, 2 or 3 if X denotes $CH_2$; and is 1, 2 or 3 if X denotes O, S, SO or $SO_2$, the process comprising reacting a tertiary alcohol of formula II

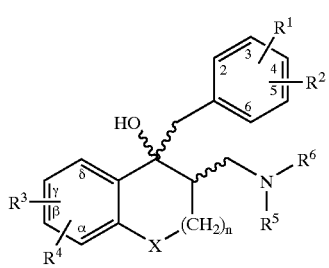

wherein $R^1$ to $R^6$, X and n are as defined above, with an acid.

14. A process according to claim 13, wherein at least one of $R^1$, $R^3$ and $R^4$ of formula II denotes O—$CH_3$, and the corresponding radicals $R^1$, $R^3$ and $R^4$ of formula IA or IB denotes OH, wherein the compound of formula II is reacted with a reagent selected from the group consisting of hydrogen bromide in glacial acetic acid, concentrated hydrobromic acid, and methanesulfonic acid and methionine.

15. A process according to claim 13, wherein the tertiary alcohol of formula II is obtained by converting a tertiary alcohol of formula III

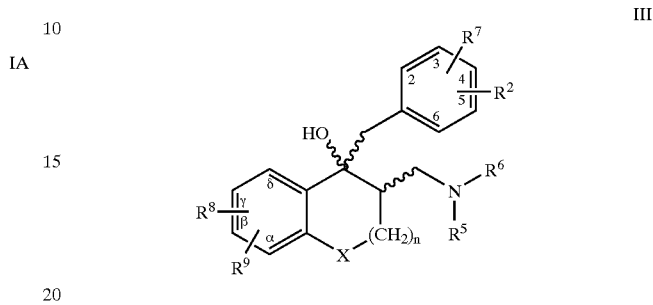

wherein $R^2$, $R^5$, $R^6$, X and n are as defined in claim 13, $R^7$ denotes H, F, Cl, O—($C_{1-6}$-alkyl), O—($C_{3-7}$-cycloalkyl), O—$CH_2$-phenyl, O—$SiR^{10}R^{11}R^{12}$, wherein $R^{10}$, $R^{11}$ and $R^{12}$ independently of one another are $C_{1-6}$-alkyl or phenyl, $CH_2F$, $CHF_2$ or $CF_3$, $R^8$ and $R^9$ independently of one another denote H, F, Cl, O—($C_{1-6}$-alkyl), O—($C_{3-7}$-cycloalkyl), O—$CH_2$-phenyl, or O—$SiR^{10}R^{11}R^{12}$, wherein $R^{10}$, $R^{11}$ and $R^{12}$ independently of one another are $C_{1-6}$-alkyl or phenyl, $CH_2F$, $CHF_2$, $CF_3$, O-aryl, aryl or heterocyclyl, and at least one of the radicals $R^7$, $R^8$ and $R^9$ is O—$CH_3$, O—($C_{2-6}$-alkyl), O—($C_{3-7}$-cycloalkyl), O—$CH_2$-phenyl or O—$SiR^{10}R^{11}R^{12}$, wherein when $R^7$, $R^8$ or $R^9$ in formula III is O—$CH_3$, O—($C_{2-6}$-alkyl), O—($C_{3-7}$-cycloalkyl), O—$CH_2$-phenyl or O—$SiR^{10}R^{11}R^{12}$, the corresponding $R^1$, $R^3$ or $R^4$ of formula II is in each case OH.

16. A process according to claim 15, wherein the tertiary alcohol of formula III is obtained by reacting a ketone of formula IV

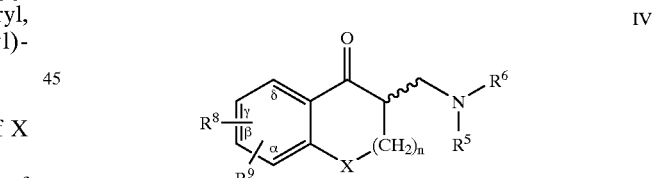

wherein $R^5$, $R^6$, $R^8$, $R^9$, X and n have the meanings given in claim 14, with an organometallic compound of formula V

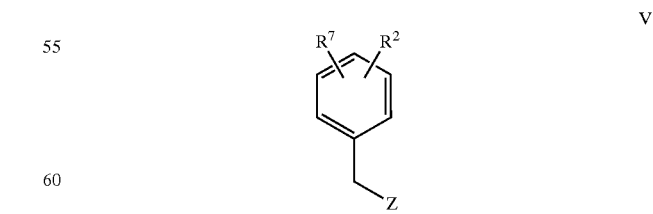

wherein $R^2$, and $R^7$ have the meanings given in claim 14, and Z denotes MgCl, MgBr, MgI or Li.

17. A process according to claim 13, wherein a compound of formula IA or IB where X=SO or $SO_2$ is obtained by oxidizing a compound of formula IA or IB where X=S.

18. A process according to claim 17, further comprising converting a compound of formula IA or IB in which at least one of $R^1$, $R^3$ and $R^4$ denotes $O-CH_3$, into compounds of formula IA or IB in which the corresponding $R^1$, $R^3$ or $R^4$ denotes OH.

19. A process according to claim 13, further comprising converting a compound of formula IA or IB in which at least one of $R^1$, $R^3$ and $R^4$ denotes $O-CH_3$, into a compound of formula IA or IB in which the corresponding $R^1$, $R^3$ or $R^4$ denotes OH.

20. A process according to claim 13, further comprising converting a free base of formula IA or IB into a pharmaceutically acceptable salt thereof.

21. A process according to claim 13, further comprising isolating the compound of formula IA or IB.

22. A process according to claim 20, further comprising isolating the pharmaceutically acceptable salt.

23. A tertiary alcohol of formula II or III

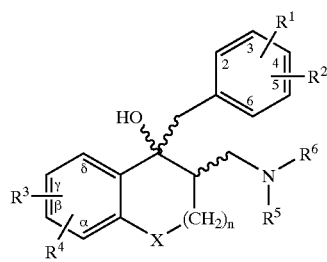

II

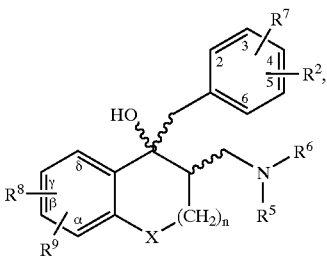

III wherein $R^1$ denotes H, F, Cl, OH, $O-(C_{1-6}$-alkyl), $O-(C_{3-7}$-cycloalkyl), $C_{1-6}$-alkyl, $CH_2F$, $CHF_2$ or $CF_3$, $R^2$ denotes H, F, Cl, $C_{1-6}$-alkyl, $CH_2F$, $CHF_2$ or $CF_3$, $R^3$ and $R^4$ independently of one another denote H, F, Cl, OH, $O-(C_{1-6}$-alkyl), $O-(C_{3-7}$-cycloalkyl), $C_{1-6}$-alkyl, $CH_2F$, $CHF_2$, $CF_3$, O-aryl, aryl or heterocyclyl, $R^5$ and $R^6$ independently of one another denote $C_{1-6}$-alkyl, $C_{3-7}$-cycloalkyl, $CH_2-(C_{3-7}$-cycloalkyl), aryl, $(C_{1-6}$-alkyl)-aryl, heterocyclyl or $(C_{1-6}$-alkyl)-heterocyclyl, $R^7$ denotes H, F, Cl, $O-(C_{1-6}$-alkyl), $O-(C_{3-7}$-cycloalkyl), $O-CH_2$-phenyl, $O-SiR^{10}R^{11}R^{12}$, wherein $R^{10}$, $R^{11}$ and $R^{12}$ independently of one another are $C_{1-6}$-alkyl or phenyl, $CH_2F$, $CHF_2$ or $CF_3$, $R^8$ and $R^9$ independently of one another denote H, F, Cl, $O-CH_3$, $O-(C_{2-6}$-alkyl), $O-(C_{3-7}$-cycloalkyl), $O-CH_2$-phenyl, $O-SiR^{10}R^{11}R^{12}$, wherein $R^{10}$, $R^{11}$ and $R^{12}$ independently of one another are $CH_3$, $C_{2-6}$-alkyl or phenyl, $CH_3$, $C_{2-6}$-alkyl, $CH_2F$, $CHF_2$, $CF_3$, O-aryl, aryl or heterocyclyl, in each case in the α-, β-, γ-and/or δ-position of the aromatic ring, and at least one of $R^7$, $R^8$ and $R^9$ is $O-CH_3$, $O-(C_{2-6}$-alkyl), $O-(C_{3-7}$-cycloalkyl), $O-CH_2$-phenyl or $O-SiR^{10}R^{11}R^{12}$, X denotes $CH_2$, O, S, SO or $SO_2$, and n is 0, 1, 2 or 3 if X denotes $CH_2$, and is 1, 2 or 3 if X denotes O, S, SO or $SO_2$.

24. A pharmaceutical composition comprising at least one compound according to claim 1, and a pharmaceutically acceptable excipient.

25. A method for the treatment of pain in a mammal in need thereof, comprising administering to the mammal a therapeutically effective amount of at least one compound according to claim 1.

26. A method according to claim 25, wherein the mammal is human.

27. A method for the treatment of urinary incontinence, itching, tinnitus aurium or diarrhea in a mammal in need thereof, comprising administering to the mammal a therapeutically active amount of at least one compound according to claim 1.

28. A method according to claim 27, wherein the mammal is human.

* * * * *